(12) United States Patent
Brouse

(10) Patent No.: US 11,766,220 B2
(45) Date of Patent: Sep. 26, 2023

(54) REJECTING NOISE IN A SIGNAL

(71) Applicant: DRÄGERWERK AG & CO. KGAA, Lübeck (DE)

(72) Inventor: Christopher J. Brouse, Cupertino, CA (US)

(73) Assignee: DRÄGERWERK AG & CO. KGAA, Lübeck (DE)

(*) Notice: Subject to any disclaimer, the term of this patent is extended or adjusted under 35 U.S.C. 154(b) by 516 days.

(21) Appl. No.: 16/923,359

(22) Filed: Jul. 8, 2020

(65) Prior Publication Data

US 2020/0367832 A1 Nov. 26, 2020

Related U.S. Application Data

(63) Continuation of application No. 15/325,682, filed as application No. PCT/US2015/046583 on Aug. 24, 2015, now Pat. No. 10,743,818.

(Continued)

(51) Int. Cl.
*A61B 5/00* (2006.01)
*A61B 5/024* (2006.01)
(Continued)

(52) U.S. Cl.
CPC .......... *A61B 5/7203* (2013.01); *A61B 5/0205* (2013.01); *A61B 5/02405* (2013.01);
(Continued)

(58) Field of Classification Search
CPC . A61B 5/7203; A61B 5/0205; A61B 5/02405; A61B 5/02416; A61B 5/0402;
(Continued)

(56) References Cited

U.S. PATENT DOCUMENTS 4,582,068 A 4/1986 Phillipps et al.
4,955,379 A 9/1990 Hall
(Continued)

FOREIGN PATENT DOCUMENTS

EP 0 913 121 5/1999
WO 2011/032132 3/2011

OTHER PUBLICATIONS

Anonymous, "Heart rate variability", Standards of measurement, physiological interpretation, and clinical use, Task Force of the European Society of Cardiology and the North American Society of Pacing and Electrophysiology, Eur. Heart J., 17:354-381 (1996).
(Continued)

*Primary Examiner* — Devin B Henson
(74) *Attorney, Agent, or Firm* — Nolte Lackenbach Siegel

(57) ABSTRACT

Reducing noise in a signal is provided. A first filter includes a selectively definable passband for filtering a first signal used in determining at least one patient parameter. A characteristic analyzer detects a characteristic of a second signal and generates a variability measurement value using a series of data values within the second signal over a previously occurring window of time. A filter controller coupled to the characteristic analyzer uses the variability measurement value to define a characteristic of the passband for the first filter and selectively tunes the passband of the first filter according to the defined characteristic. Related apparatus, systems, techniques, and articles are also described.

17 Claims, 11 Drawing Sheets

Related U.S. Application Data

(60) Provisional application No. 62/041,313, filed on Aug. 25, 2014.

(51) Int. Cl.
*A61B 5/318* (2021.01)
*A61B 5/0205* (2006.01)
*A61B 5/1455* (2006.01)

(52) U.S. Cl.
CPC ...... *A61B 5/02416* (2013.01); *A61B 5/14551* (2013.01); *A61B 5/318* (2021.01); *A61B 5/721* (2013.01); *A61B 5/725* (2013.01); *A61B 5/7225* (2013.01)

(58) Field of Classification Search
CPC ... A61B 5/14551; A61B 5/721; A61B 5/7225; A61B 5/725
See application file for complete search history.

(56) References Cited

U.S. PATENT DOCUMENTS

| 5,971,930 | A | 10/1999 | Elghazzawi |
| 9,408,542 | B1* | 8/2016 | Kinast ................. A61B 5/7246 |
| 9,999,359 | B2* | 6/2018 | Thakur ................ A61B 5/7282 |
| 2012/0190948 | A1 | 7/2012 | Vetter et al. |
| 2013/0116580 | A1 | 5/2013 | Liu et al. |

OTHER PUBLICATIONS

Barbieri et al., "A point-process model of human heartbeat intervals: new definitions of heart rate and heart rate variability," Am. J. Physiol. Heart Circ. Physiol., 288:H424-H435 (2005).

International Search Report for Application No. PCT/US2015/046583, dated Oct. 30, 2015.

International Preliminary Report on Patentability for International Application No. PCT/US2015/046583, dated Mar. 9, 2017.

* cited by examiner

REJECTING NOISE IN A SIGNAL

CROSS-REFERENCE TO RELATED APPLICATION

This application is a continuation of U.S. application Ser. No. 15/325,682, filed Jan. 11, 2017, which is a national stage application, filed under 35 U.S.C. § 371, of International Application No. PCT/US2015/046583, filed Aug. 24, 2015, which claims priority under 35 U.S.C. § 119(e) to U.S. provisional patent application No. 62/041,313, filed Aug. 25, 2014, the entire contents of each of which are hereby expressly incorporated by reference in its entirety.

TECHNICAL FIELD

The subject matter described herein relates to electronic devices and, more particularly, to an improved system for rejecting noise in a signal sensed by a sensor and used in determining a physiological parameter of a patient.

BACKGROUND

The use of electronic devices to perform any number of tasks has steadily increased over time. This is especially true in the field of providing healthcare to patients. In the medical field, patient monitoring devices and/or systems are selectively coupled to a patient via at least one sensor, which senses information from the patient and is used in deriving at least one physiological parameter associated with the patient.

One type of patient monitoring device is a pulse oximeter. A pulse oximeter measures arterial blood oxygen saturation ($SpO_2$) and pulse rate (PR) using principles of light transmission and absorption and generates a photoplethysmogram (PPG) signal. The pulse oximeter uses a sensor affixed to one of a predetermined position of the patient. Examples of predetermined positions on patients to which a pulse oximeter may be affixed includes, but is not limited to, a finger, foot, earlobe, toe, cheek, nose, nasal alar, scalp, wrist and torso. The sensor typically contains at least two light emitting diodes (LEDs) and a photodiode detector. The LEDs emit light at red (~660 nm) and infrared (~880 nm) wavelengths, some of which is absorbed by the patient's tissues and fluids, and some of which reaches the photodiode detector. The above described wavelengths of light emitted by the LEDs is described for purposes of example only and, in operation, the LEDs may emit light at any wavelength that falls within the red region and infrared region. More generally, it is possible the LEDs may emit light at two different wavelengths even outside the red and infrared regions. Furthermore, multi-LED sensors may measure at additional wavelengths outside the red and infrared regions. Oxygenated and deoxygenated hemoglobin absorb red and infrared light differently. Changing blood oxygen concentration changes the relative absorption at the two wavelengths. The acquired red and infrared signals can then be analyzed to measure the blood oxygenation. The greater the tissue and fluid between the emitters and detector, the less red and infrared light that reaches the detector. As a result, the measured PPG signals contain a constant (DC) component and a pulsatile (AC) component. The DC component results from the fixed absorbers, including skin, muscle, fat, bone, and venous blood. The AC component results from the periodic pulsations of the heart, driving changes in arterial blood volume. The PR can be measured from the PPG by detecting pulse peaks, and counting their number over a fixed time period (e.g., 60 s). The SpO2 can be measured by calculating the ratio of AC to DC components in both the red and infrared signals, which is commonly referred to as the "ratio of ratios" R and is illustrated below in Equation 1.

$$R=(AC_r/DC_r)/(AC_{ir}/DC_{ir}) \quad (1)$$

The resulting value R determined in Equation 1 is used to look up the $SpO_2$ value in an experimentally-determined reference table as is known in the art. Equation 1 is provided for the purposes of example only and, in operation, an oximeter may use a different method of calculating $SpO_2$.

A drawback associated with PR and $SpO_2$ values determined by the pulse oximeter is their susceptibility to noise present in the signal being measured. Types of noise that may be present in the signal being measured may include any of (a) electronic noise; (b) ambient light; (c) electrocautery noise and (d) any other type of noise from any source. The following illustrates an example where the noise present is electronic noise. However, it should not be construed to mean that the signal includes only a single type of noise. The signal may in fact include a plurality of different types of noise at any given time depending on the environmental conditions surrounding the pulse oximeter.

Analog electronic components introduce noise into the measured PPG signal. Noise corrupts the LED signal that is transmitted through the patient's tissue. When the patient's tissue is very opaque (e.g. when the sensor site is a thick appendage like a neonatal foot, or when the skin has dark pigmentation) most of the LED signal is absorbed in the tissue and only a weak signal is received by the oximeter circuit. The receiver circuit can compensate for a weak signal by amplifying it; however, the signal and noise are amplified together. To make matters worse, the act of amplifying the signal introduces additional noise. Indeed, most filtering and amplification operations performed in analog circuitry introduce additional noise into the measured signal. This decreases the signal-to-noise ratio (SNR). Thus, because the signal AC component is typically a very small fraction of the overall measured signal (often on the order of 1% or less), the AC signal may easily be obscured or overcome with noise resulting in an incorrect measurement of the AC component. This noise makes it more difficult for digital signal processing to estimate the PR and SpO2 because the AC values ($AC_r$ and $AC_{ir}$) used in Equation 1 would be less accurate. Incorrect measures lead to false alarms and contribute to the clinical problem of alarm fatigue, wherein clinicians become desensitized to overactive alarms. It is thus highly desirable to remove noise from the measured PPG signals, to improve patient monitoring.

The noise can be decreased and the SNR can be increased by narrowing the signal bandwidth. Some noise may be white (that is, constant across all frequencies), such as that introduced by resistive circuit elements. Other noise may have a 1/f distribution (that is, the noise becomes less powerful with increasing frequency), such as that introduced by active semiconductor circuit elements. In either case, the noise can be approximated as white since the PPG bandwidth of interest is very narrow, typically no more than ~5 Hz. The power of white noise increases with the square root of the signal bandwidth. If the signal bandwidth can be reduced by a factor of four, the noise will be reduced by a factor of two.

SUMMARY

In one aspect, an apparatus for reducing noise in a signal is provided. A first filter includes a selectively definable passband for filtering a first signal used in determining at least one patient parameter. A characteristic analyzer detects a characteristic of a second signal and generates a variability measurement value using a series of data values within the second signal over a previously occurring window of time. The series of data values within the second signal includes past values of the detected characteristic of the second signal over a previously occurring window of time. A filter controller coupled to the characteristic analyzer uses the variability measurement value to define a characteristic of the passband for the first filter and selectively tunes the passband of the first filter according to the defined characteristic.

In another aspect, a method of reducing noise in a signal is provided. The method includes selectively defining a passband of a first filter for filtering a first signal used in determining at least one patient parameter and detecting, by a characteristic analyzer, a characteristic of a second signal. A variability measurement value is generated using a series of data values within the second signal over a previously occurring window of time and a filter controller uses the variability measurement value to define a characteristic of the passband for the first filter. The passband of the first filter is selectively tuned according to the defined characteristic of the passband.

One or more of the following features can be included in any feasible combination. For example, the characteristic analyzer can continually generate the variability measurement values over successive time intervals and the filter controller continually adjusts the passband of the first filter. The characteristic of the second signal detected can be associated with the at least one patient parameter. The characteristic of the passband can include at least one of (a) a center frequency for the passband; (b) a width of a frequency envelope for the passband; (c) lower and upper cutoff frequencies for the passband; and (d) a shape of the frequency envelope for the passband. The characteristic of the passband can include data representing a guard band that expands the width of the passband.

A first sensor can sense the first signal from a patient. A second sensor can sense the second signal from the patient. The second sensor can be independent from the first sensor. A parameter processor can be coupled to each of the characteristic analyzer and the first filter. The parameter processor can use the filtered first signal to determine the at least one patient parameter. The parameter processor can compare the at least one patient parameter with the characteristic of the second signal to determine a signal quality index (SQI) measurement. The characteristic analyzer can selectively modify at least one parameter of the characteristic analyzer used in determining the variability measurement value when the comparison indicates the SQI measurement is below a threshold value. The first signal can be a photoplethysmogram (PPG) signal. The at least one patient parameter can include at least one of a pulse rate (PR) of a patient and a blood oxygen saturation level (SpO2) of a patient. The second signal can include an electrocardiogram (ECG) signal.

The first filter can filter a signal measured from light at a first wavelength. A second filter can filter a signal measured from light at a second wavelength. The second wavelength can be greater than the first wavelength. The passband for each of the first filter and the second filter can be adjusted using the filter parameter generated by the filter controller. The variability measurement of the second signal can represent a heart rate variability (HRV) over a predetermined period using a heart rate variability measurement technique. The characteristic analyzer can determine the heart rate variability (HRV) using at least one of (a) a time domain measurement technique; (b) a frequency domain measurement technique; (c) a joint time-frequency domain measurement technique; (d) a nonlinear dynamic measurement technique; and (e) any other type of HRV measurement technique.

The characteristic of the second signal can be a heart rate (HR) derived from the ECG signal. The variability measurement value can represent a heart rate variability (HRV) over a predetermined prior period. The parameter processor can determine signal quality index (SQI) by calculating a pulse rate variability (PRV) over the predetermined period window and comparing the pulse rate variability to the heart rate variability. The passband of the first filter represents a frequency of heart beats.

The variability measurement values can be continually generated over successive time intervals. The passband of the first filter can be continually adjusted, by the filter controller. The characteristic of the second signal detected can be associated with the at least one patient parameter. The activity of defining the characteristic of the passband can include at least one of (a) defining a center frequency for the passband; (b) defining a width of a frequency envelope for the passband; (c) defining lower and upper cutoff frequencies for the passband; and (d) defining a shape of the frequency envelope for the passband. The activity of defining the characteristic of the passband can include generating data representing a guard band that expands the width of the passband and expanding the width of the passband of the first filter using the data representing the guard band.

The first signal from a patient can be sensed via a first sensor. The second signal from the patient can be sensed via a second sensor. The second sensor can be independent from the first sensor. The filtered first signal can be used, by a parameter processor, to determine the at least one patient parameter. The at least one patient parameter can be compared by the parameter processor with the characteristic of the second signal to determine a signal quality index (SQI) measurement. At least one parameter of the characteristic analyzer used in determining the variability measurement value can be selectively modified when the comparison indicates the SQI measurement is below a threshold value.

A signal measured from light at a first wavelength can be filtered via the first filter. A signal measured from light at a second wavelength can be filtered via a second filter. The second wavelength can be greater than the first wavelength. The passband can be adjusted for each of the first filter and the second filter using the at least one filter parameter generated by the filter controller. The variability measurement of the second signal can represent a heart rate variability (HRV) over a predetermined period. The heart rate variability (HRV) can be determined by the characteristic analyzer using at least one of (a) a time domain measurement technique; (b) a frequency domain measurement technique; (c) a joint time-frequency domain measurement technique; (d) a nonlinear dynamic measurement technique; and (e) any other type of HRV measurement technique.

A signal quality index (SQI) can be determined by the parameter processor. A pulse rate variability (PRV) over the predetermined period window can be calculated and the pulse rate variability can be compared to the heart rate variability. The passband of the first filter can represent a frequency of heart beats.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
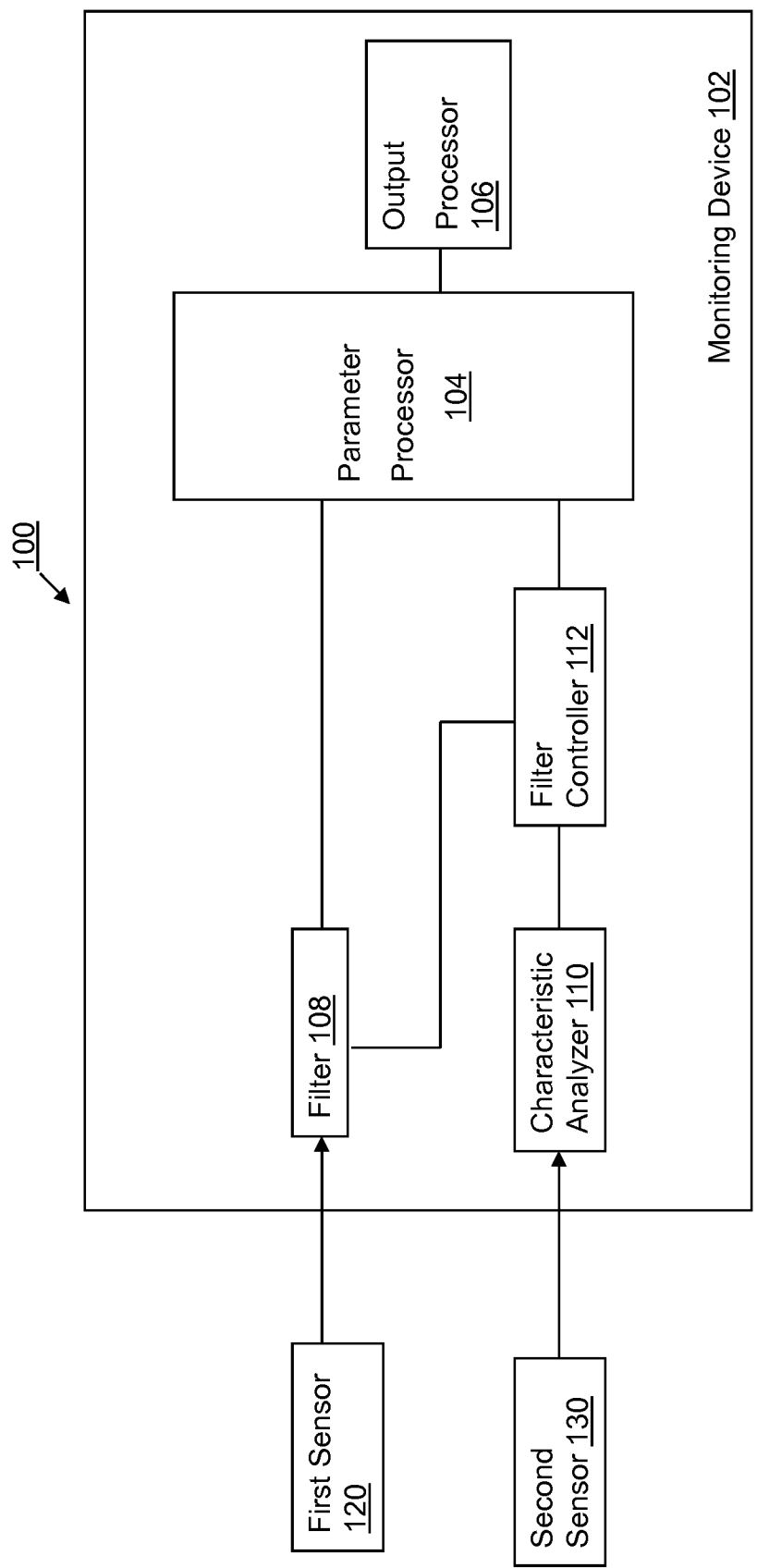
FIG. 1 is a block diagram of a device for reducing noise in a signal.

Some aspects of the current subject matter describe a filtering approach to remove noise and improve the SNR. A system according to some aspects of the current subject matter addresses the deficiencies associated with deriving patient parameters from a signal sensed by a sensor.

Reducing electronic noise in a signal sensed by a patient connected sensor is provided. In some implementations, an apparatus advantageously senses a first signal from a patient and suppresses noise introduced into the first signal using a characteristic derived from a second signal, which is correlated in frequency to the first signal, sensed by a second patient connected sensor to dynamically tune (e.g., set) parameters of a filter that filters the first sensed signal. The noise introduced in the first signal may include at least one of (a) electronic noise; (b) ambient light; (c) electrocautery noise; and (d) any other type of noise from any source. Additionally, as used herein, dynamically tuning a filter includes the activity of dynamically and in real-time using a characteristic to modify at least one characteristic of the filter to define a range of frequencies to at least one of (a) be passed therethrough; and (b) be excluded thereby. The characteristic used to dynamically tune a filter for filtering the first sensed signal may be based on a variability parameter derived from a series of instantaneous data values from the second signal and is associated with a portion of the first signal that is of interest for determining at least one type of patient parameter.

The filter may include a definable passband which refers to a range of frequencies of a particular signal that are allowed to pass through the filter for further processing thereof. Moreover, the passband may be tuned using the characteristic derived from the second signal. The dynamic tuning of the filter occurs by determining a frequency envelope associated with the passband and which is based on the value of the characteristic and controlling the filter to allow signals having frequency content within the envelope to pass therethrough while excluding signals having frequency content outside of the envelope (e.g. higher or lower frequencies). Because the characteristic is associated with the interested portion of the first signal, the determined envelope is narrow enough to maximize the amount of noise suppressed while minimizing the chance that a signal portion of interest will be excluded. In one implementation, dynamically tuning the filter may include defining a characteristic of a passband of the filter by setting at least one of (a) a center frequency for the passband; (b) a width of the passband; and (c) a shape of the passband.

In another implementation, dynamically tuning the filter may include at least one of (a) adjusting a center frequency of the filter; (b) adjusting an upper cutoff frequency for the filter; and (c) adjusting a lower cutoff frequency of the filter. Moreover, by dynamically tuning the filter as discussed above, the apparatus may automatically modify the parameters used to tune the filter on a period-by-period basis. This advantageously enables tuning of the filter to occur on a rolling basis thereby taking advantage of any changes in the characteristic derived from the second signal to improve the suppression of any noise in the first signal. By dynamically tuning a filter using the characteristic, the apparatus advantageously achieves a balance between maximizing the passage of the valid component of the first sensed signal and minimizing the passage of in-band noise.

An exemplary apparatus 100 for reducing noise in a signal is provided in FIG. 1. The exemplary apparatus 100 of FIG. 1 may be a patient monitoring device 102 having a first type of patient connected sensor 120 that senses a first type of signal from the patient. A second type of patient connected sensor 130 that senses a second type of signal from the patient is also connected to the patient monitoring device 102.

The patient monitoring device 102 includes a parameter processor 104 for selectively processing the first type of signal and the second type of signal to determine a plurality of different patient parameters. The parameter processor 104 represents circuitry that is specifically conditioned to execute at least one type of patient parameter processing algorithm that uses data contained in the first type of signal and second type of signal to derive respective types of patient parameter data that may be output to a clinician via an output processor 106. The output processor 106 may receive and format for display the patient parameter data determined by the parameter processor 104. In another implementation, the output processor 106 may comprise communication functionality and generate a message including the patient parameter data. The output processor 106 selectively connects to a communication network to communicate the message to a remote system (e.g. a healthcare information system, a central monitoring station, etc.). Once communicated, the patient parameter data in the message may be used by a clinician to support the delivery of healthcare to the patient.

To derive the patient parameter data used in supporting the delivery of healthcare to a patient, the patient monitoring device 102 includes a plurality of components that process and/or modify the signals sensed by the first type of sensor 120 and second type of sensor 130. The patient monitoring device 102 includes at least one filter 108 that filters the first type of signal to exclude all components outside of a predetermined frequency band, allowing only an interested portion of the first type of signal to be provided to the parameter processor 104 for use in determining the patient parameter data. Because the apparatus minimizes noise contained in the first type of signal, it is desirable to determine a frequency envelope that is narrow enough to exclude as much of the noise as possible but wide enough to ensure that the filtered signal being provided to the parameter processor 104 includes all information that is relevant for determining the patient parameter data. The determination of the frequency envelope is advantageously accomplished using a characteristic derived from the second type of signal, which is correlated in frequency to the first signal, sensed by the second sensor 130.

The patient monitoring device 102 includes a characteristic analyzer 110 that derives, from the second type of signal, a characteristic known to be associated with the interested portion of the first type of signal. The characteristic is a variability measurement representing the variability of a type of data over a predetermined period prior to the determination thereof by the characteristic analyzer 110. In one implementation, the predetermined period may represent a number of individual data values. In another implementation, the predetermined period may represent a period of time. The characteristic analyzer 110 generates a variability measurement that is provided to a filter controller 112. The filter controller 112 translates the variability measurement into a filter control parameter used to control the at least one filter 108 by establishing a bandwidth envelope defining the passband for the filter 108. The bandwidth envelope includes an upper bound and lower bound enabling signals having a frequency between the upper and lower bounds to pass therethrough. In one implementation, the bandwidth envelope established by the filter control parameter may also include a guard band. The guard band represents an increase in frequency range above the upper bound and below the lower bound of the envelope to minimize the chance of excluding a relevant signal. In another implementation, the guard band may increase the frequency range above the upper bound. Alternatively, the guard band may decrease the frequency range below the lower bound. To generate the guard band, the filter controller 112 automatically modifies the filter control parameter determined based on the variability measure to increase the width of the envelope to compensate for any errors in the variability measure determined by the characteristic analyzer. Thus, in real time, at each interval, the characteristic analyzer 110 may determine the variability measure that is used to continually determine and modify, as needed, the filter parameter used to define the frequency envelope of the filter 108. Thus, at each interval at which the first signal is sensed by the first sensor 120, the filter 108 is automatically configured to include a passband to catch signals that are relevant in determining the patient parameter data. The variability measure used in configuring the frequency envelope is associated with the patient parameter data being determined by the parameter processor 104. Moreover, as this configuration occurs in real time and at each measurement interval (e.g. rolling configuration), the patient monitoring device 102 advantageously suppresses the noise contained in the first type of signal by excluding those signals which have a frequency outside the frequency envelope.

While the exemplary apparatus 100 of FIG. 1 is described as a single patient monitoring device, one skilled in the art will understand that components described herein may be implemented in multiple devices that are able to communicate with one another via a communication network. Alternatively, these two devices may be connected to a single docking station and the communication therebetween may be facilitated by the docking station.

Additionally, the description of the patient monitoring device including a single filter 108 is shown for purposes of example only and is described to illustrate the principles of the current subject matter. However, the patient monitoring device 102 may have a plurality of filters that may be used to filter different portions of the first type of signal. For example, if the first sensor 120 senses multiple signals, the patient monitoring device 102 may include a number of filters 108 equal to the number of signals sensed by the first sensor 120. Each of these filters may be selectively controlled using the filter parameter generated by the filter controller 112 based on the variability measurement.

Figure 2:
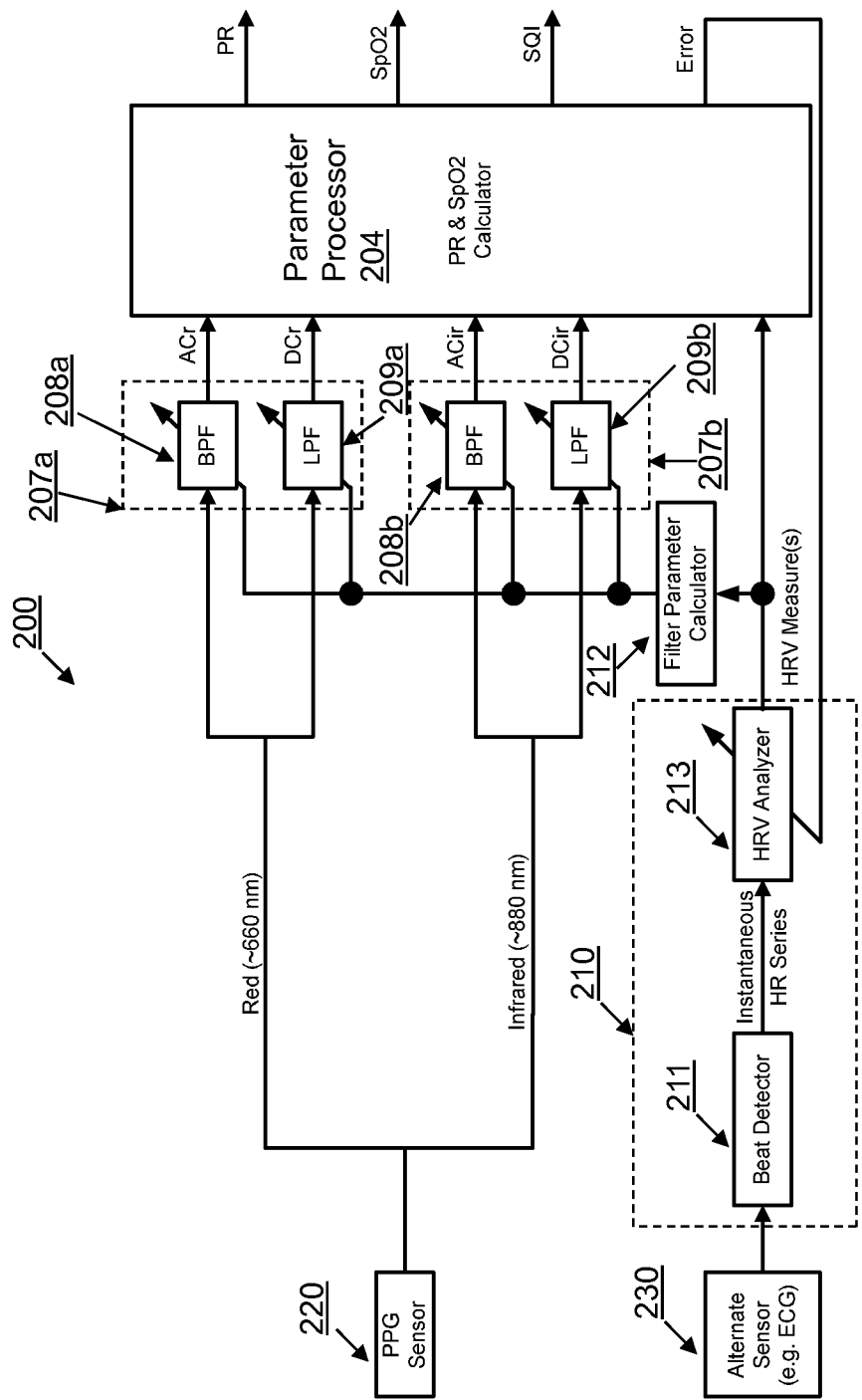
FIG. 2 is a block diagram of device for reducing noise in a signal.
Figure 4:
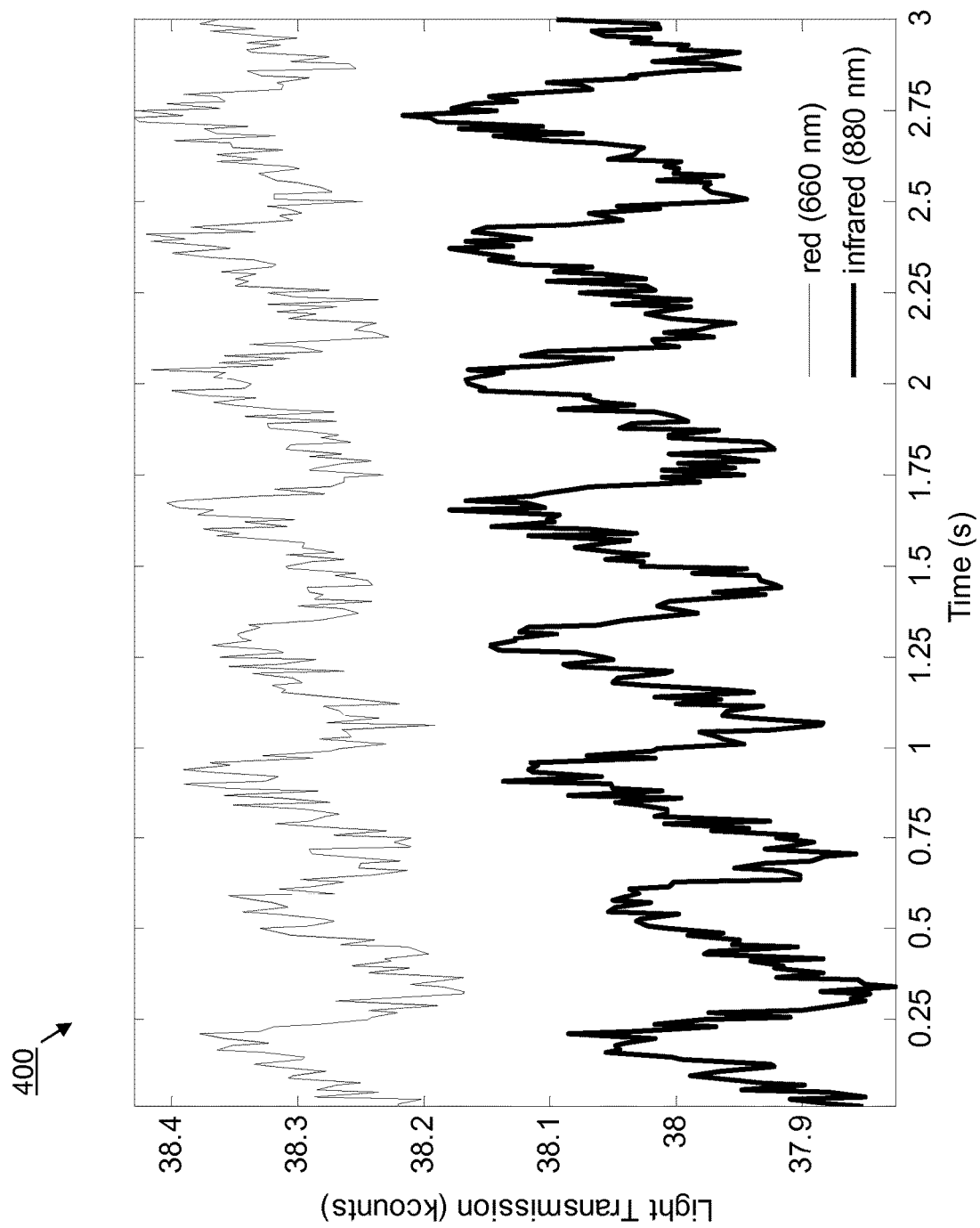
FIG. 4 is a graph depicting an exemplary signal in which noise may be reduced using the algorithm in FIG. 3.

An exemplary patient monitoring device described in FIG. 1 is illustrated in greater detail in FIG. 2. FIG. 2 depicts a patient monitoring device 200 wherein the first sensor is a pulse oximeter 220 that senses a first signal representing a photoplethysmogram (PPG). The PPG signal includes a signal measured from light sensed at a first wavelength (e.g. red light at substantially 660 nm) and a signal measured from light sensed at a second wavelength (e.g. infrared light at substantially 880 nm). The patient monitoring device 200 includes a first set of filters 207a for filtering the signal from light of the first wavelength and a second set of filters 207b for filtering the signal from light of the second wavelength. The first and second set of filters 207a, 207b each include a bandpass filter (BPF) 208a and 208b, respectively, and a low pass filter (LPF) 209a and 209b, respectively. The portion of the signal filtered by the bandpass filters 208a, 208b produce an AC component. Therefore, as there are two different signals/wavelengths sensed by the pulse oximeter 220, bandpass filter 208a generates an AC component associated with light of the first wavelength ($AC_r$) and bandpass filter 208b generates an AC component associated with light of the second wavelength ($AC_{ir}$). Signals from light of the first wavelength and second wavelength are also filtered by the low pass filters 209a, 209b to generate DC components. The output of the low pass filter 209a is a DC component associated with the signal from light of the first wavelength ($DC_r$) and the output of the low pass filter 209b is a DC component associated with the signal from light of the second wavelength ($DC_{ir}$). The values of $AC_r$, $AC_{ir}$, $DC_r$ and $DC_{ir}$ are provided to the parameter processor 204 which determines patient parameter data representing an $SpO_2$ value and a PR value for the patient at a given time. An exemplary plot 400 of the signal from light of the first wavelength and the signal from light of the second wavelength is shown in FIG. 4. In FIG. 4, the PPG signal is measured from the foot of a neonatal patient. The signal is weak and corrupted by strong electronic noise (i.e. it has a low SNR). It is difficult to accurately measure PR and $SpO_2$ during such periods of low SNR without advanced filtering techniques.

It is highly desirable to control the filter parameters used in defining a frequency envelope of bandpass filters 208a and 208b for filtering the signals from light of the first and second wavelengths to improve the accuracy of the determined PR and $SpO_2$. To control the filter parameters, the patient monitoring device 200 also senses a second signal representing an electrocardiogram (ECG) signal via a plurality of patient-connected electrodes 230. The second sensor (i.e., the plurality of patient-connected electrodes) 230 sensing a second signal representing an ECG signal is described for purposes of example only and the second signal may include any type of signal that can be correlated in frequency to the first signal. Examples of other types of second signals include any of (a) invasive arterial blood pressure (IBP or ABP) signals; (b) ballistocardiogram (BCG) signals; (c) a second PPG signal derived from a pulse oximeter positioned at a different location than the pulse oximeter that generates the first signal; and (d) any other type of signal that can be correlated in frequency to the first signal. It is further desirable that the second signal is derived independently from the first signal to further improve the reliability. The electrical impulses sensed by the ECG electrodes are provided to the characteristic analyzer 210. The characteristic analyzer 210 includes a beat detector 211 that analyzes the electrophysiological data sensed by the electrodes and determines an instantaneous heart rate (HR) series. The characteristic analyzer also includes a heart rate variability (HRV) analyzer 213 that uses the instantaneous HR series data over an immediately preceding period to determine an HRV measure representing the variability of the patient's HR over the prior period. The immediately preceding period may be referred to as the analysis window or variability window. The HRV measurement value output by the HRV analyzer 213 is provided to the filter controller 212 which calculates a filter parameter using the HRV measure. The filter parameter controls represent a frequency envelope and are used to tune the bandpass filters 208a and 208b to define the passband of each bandpass filter 208a and 208b. This advantageously enables the device to dynamically tune the filter(s) in real-time based on a characteristic known to be correlated with the portion of the first signal that is of interest and used to determine both the PR and the $SpO_2$ of the patient.

By using the HRV measure derived by the HRV analyzer 213 to tune the passband of the BPF, a filtering balance between maximizing the valid pulse frequency content and minimizing the in-band noise may be achieved. Moreover, it is understood that the relevant information in the PPG component (signals from red and infrared light) that is used by the parameter processor 204 in determining a PR value and a $SpO_2$ value exists at or near the HR frequency. Thus, the characteristic of the second signal (HR and HRV) is associated with the portion of the first signal (PPG) that is of interest when determining patient parameter data.

HRV is a term to describe variations of both instantaneous heart rate and RR intervals. The HRV is a reflection of the subject's autonomic state. There are many different causes of variation in a patient's HR over time. One cause may result from a patient changing from a state of health/relaxation to one of disease/stress, thereby changing the HR pattern. Additionally, the HR of a patient may fluctuate in a high frequency band (HF, 0.15-0.4 Hz). This fluctuation, called respiratory sinus arrhythmia (RSA), is a healthy heart arrhythmia. Another phenomenon known as baroreflex may cause the HR to fluctuate in a low frequency band (LF, 0.04-0.15 Hz). One example of this is a Meyer wave which causes low frequency (~0.1 Hz) fluctuations and is especially common among pediatric subjects under high stress. Finally, long-term cycles such as the circadian rhythm may cause HR fluctuations in a very low frequency band (VLF, <0.04 Hz). Other terms that may be used to describe oscillation in consecutive cardiac cycles includes, for example, cycle length variability, heart period variability, heart period variability, RR variability, and RR interval tachogram.

Figure 5:
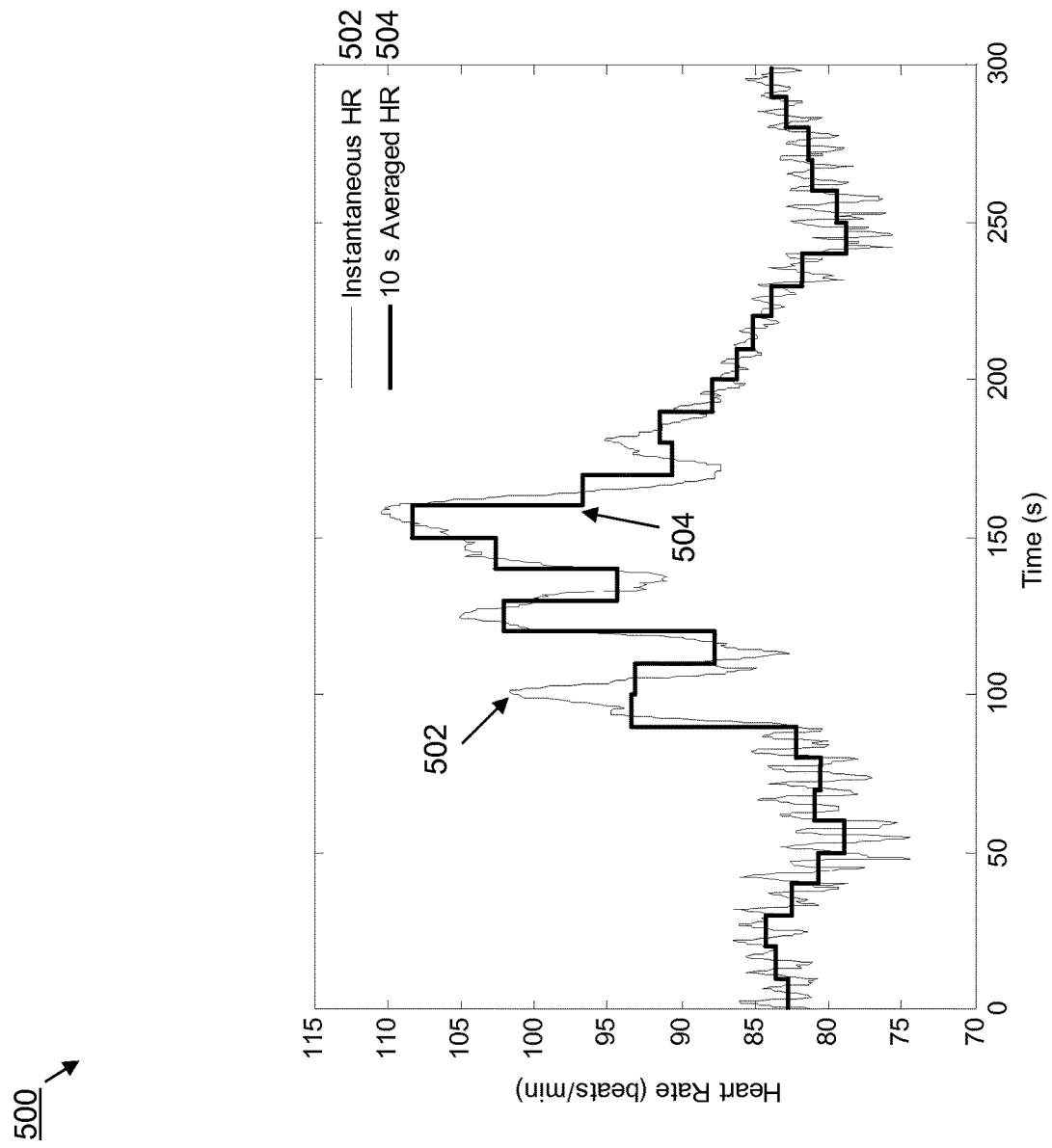
FIG. 5 is a graph depicting instantaneous heart rate plotted against an average heart rate over a period of time.

To compensate for these and other phenomena that cause variation in the HR of the patient, the beat detector 211 generates a series of data values representing instantaneous HR data. The instantaneous HR data values represent normal-to-normal (NN) heartbeat intervals, which are those intervals between adjacent heartbeats resulting from sinus node depolarization. NN intervals reflect the autonomic state. The instantaneous HR data values may also include abnormal beats that result from other causes (e.g. premature ventricular beats, premature atrial beats, nodal premature beats, bundle branch block beats, supraventricular premature or ectopic beats, R-on-T premature ventricular contractions, fusion of ventricular and normal beats, atrial escape beats, nodal escape beats, supraventricular escape beats, ventricular escape beats, paced beats, fusion of paced and normal beats, etc.). Only the NN heartbeat intervals reflect the autonomic state, and other beats are typically excluded from HRV analysis. However, the present system is concerned with measuring the frequency of heart beat pulses. If an abnormal (non-autonomic) heartbeat produces a pulse, then it will be manifested in the PPG signal and should be used in the HRV calculation. Thus, the beat detector 211 advantageously characterizes all beats regardless of their origin. The parameter processor 204 configures a window used by the HRV analyzer 213. The window represents the predetermined period of instantaneous HR data to be analyzed by the HRV analyzer 213. In one implementation, the predetermined period may be set equal to 10 seconds because the HR can vary widely in a typical ~10 s window based on the presence of multiple cycles of respiration-driven fluctuations (RSA). For example, in an adult patient breathing slowly at 12 breaths per minute, two RSA cycles would occur in a 10 second window whereas in a neonatal subject breathing quickly at 30 breaths per minute, the window would contain 5 RSA cycles. The window may also contain approximately one cycle of lower frequency fluctuations. This is particularly true in pediatric subjects, who are prone to exhibiting Meyer waves at ~0.1 Hz. Thus, in contrast to simply averaging the instantaneous HR data over the window and using the average value, the HRV analyzer 213 advantageously maintains the information associated with instantaneous fluctuations of the patient HR allowing those variations to better tailor the bandwidth envelope of bandpass filters 208a and 208b. The difference between a typical 10 s averaged HR series and its instantaneous HR counterpart is illustrated in plot 500 of FIG. 5. Therein, it is readily apparent that using an average HR illustrated by line 502 as compared to the instantaneous HR counterpart illustrated in line 504, would require the bandwidth envelope of the bandpass filters 208a and 208b to be either unreasonably large (conservative) thereby including undesirable noise, or unreasonably narrow (aggressive) thereby excluding pulsatile information that is relevant in determining the PR and SpO$_2$ value for the patient. A critical concern is that the HRV is not constant in time or across subjects and the frequencies and amplitudes can vary widely. Therefore, without factoring the HRV into defining the boundaries of the bandwidth envelope for the bandpass filter 208a and 208b, there is an increased risk of either passing undesired in-band noise or rejecting valid pulsatile information from the PPG signal resulting in less accurate PR and SpO$_2$ values generated by the parameter processor 204.

The HRV analyzer 213 advantageously generates an HRV measure according to at least one type of HRV measurement technique. HRV measurement techniques able to be implemented by the HRV analyzer 213 include at least one of (a) a time domain measurement technique; (b) a frequency domain measurement technique; (c) a joint time-frequency domain measurement technique; (d) a nonlinear dynamic measurement technique; and (e) any other type of HRV measurement technique. The listed techniques are not meant to be construed as limiting and any algorithmic technique able to measure HRV may be employed by the HRV analyzer. As used herein, the term technique represents a type of algorithm executable by the HRV analyzer 213 circuitry.

In one implementation, the HRV analyzer 213 may determine the HRV measurement value by analyzing the instantaneous HR series data in the time domain. Generally, the time domain measurement techniques apply a statistical analysis of the NN intervals or difference between NN intervals. One example of a statistical analysis applied in the time domain is the standard deviation of NNs (SDNN) which estimates the overall variability of the HR. The overall variability of the HR is linked to autonomic state, with increased variability associated with states of health/relaxation, and decreased variability associated with states of disease/stress. SDNN is typically used in analysis windows 5 minutes long; however, the method continues to function even when the window is decreased to 1 min and possibly even shorter, since the present HRV analysis is not being used to measure autonomic state of the patient but rather the variation of frequencies associated with all HR pulses within the window. In some example implementations, the HRV analyzer 213 receives the instantaneous HR series from the beat detector 211 and computes the HRV as the standard deviation of a predetermined number of samples (or length of time). Another example of a statistical analysis applied to generate an HRV measurement value is the root mean square of successive differences between NNs (RMSSD). RMSSD estimates the short term high frequency variation in the HR. Though widely used, RMSSD can be combined with other algorithms for the purposes of the current subject matter. It can be desirable for the HRV analyzer 213 (in addition to the high frequency variations from RMSSD), as all HRV frequencies can be important in some implementations. In some example implementations, the HRV analyzer 213 receives the instantaneous HR series from the beat detector 211 and computes the HRV as the root mean square of the beat-to-beat changes in the HR series over a predetermined number of samples (or length of time). The root mean square for n samples may be computed according to:

$$x_{rms} = \sqrt{\frac{1}{n}(x_1^2 + x_2^2 + \ldots + x_n^2)}$$

where $x_i$ represent the difference between two successive HR samples.

Implementations of SDNN and RMSSD for the purposes of the current subject matter would be expanded to additionally process non-NN intervals, since some implementations of the present subject matter can measure the variability of the HR rather than the patient's autonomic state. A further example of a time domain measurement technique involves point process modeling. Point process modeling models the HR samples as random variables drawn from a statistical point process. The random variables have been modeled using the Inverse Gaussian distribution, whose parameters are estimated from the recent history of beat times. The parameters are continually updated with new estimations each time a new beat occurs. In some example implementations, the HRV analyzer 213 receives the instantaneous HR series from the beat detector 211 and computes the inverse Gaussian distribution parameters (e.g., mean and shape). The HRV can be determined from the inverse Gaussian distribution, which can be described by:

$$pdf = \left[\frac{\lambda}{2\pi x^3}\right]^{\frac{1}{2}} \exp\left(\frac{-\lambda(x-\mu)^2}{2\mu^2 x}\right)$$

where μ represents the mean, and λ represents the shape parameter. The maximum likelihood estimate of the standard deviation may be used as the HRV.

In some implementations, the point process modeling can include a history-dependent inverse Gaussian (HDIG) point process. With HDIG, it is assumed that given any R-wave event $\lambda_k$, the waiting time until the next R-wave event (e.g., the length of the next R-R interval) obeys an HDIG probability density described by:

$$pdf = \left[\frac{\theta_{p+1}}{2\pi(t-u_k)^3}\right]^{\frac{1}{2}} \exp\left(\frac{-\theta_{p+1}(t-u_k-\mu(H_k,\theta))^2}{2\mu(H_{u_k},\theta)^2(t-u_k)}\right)$$

where $H_k=(u_k, w_k, w_{k-1}, \ldots, w_{k-p+1})$, $w_k=u_k-u_{k-1}$ is the k$^{th}$ R-R interval, $\mu(H_k,\theta)=\theta_0+\Sigma_{j=1}^{P}\theta_k w_{k-j+1}>0$ is the mean, $\theta_{p+1}>0$ is the scale parameter, and $\theta=(\theta_0, \theta_1, \ldots, \theta_{p+1})$ is a vector of time-varying model parameters. HRV may be one or more of the maximum likelihood estimate of the standard deviation of the R-R interval or the heart rate. Given the maximum likelihood estimate of $\theta_t$, the maximum likelihood estimate of the standard deviation of the R-R interval and the heart rate is given respectively by:

$$\hat{\sigma}_{RR_t} = \left[\mu(H_{u_k},\hat{\theta}_t)^3 \hat{\theta}_{p+1,t}^{-1}\right]^{\frac{1}{2}}$$

$$\hat{\sigma}_{HR_t} = \left[\frac{2\mu_t^*(H_t,\hat{\theta}_t) + \hat{\theta}_{p+1,t}^*}{\mu_t^*(H_t,\hat{\theta}_t)\hat{\theta}_{p+1,t}^{*2}}\right]^{\frac{1}{2}}$$

The point process modeling method advantageously can convert a discrete, unevenly sampled signal (the HR series) into a continuous time signal with arbitrary resolution enabling estimation of HRV parameters between beats. Moreover, the point process modeling technique advantageously can predict the time of the next heartbeat, which allows the HRV analyzer 213 and filter controller 212 to better tune BPF parameters in advance of upcoming pulses.

In another implementation, the HRV analyzer 213 may determine the HRV measurement value by analyzing the instantaneous HR series data in the frequency domain. Performing a frequency domain analysis advantageously reveals an underlying structure to the HR series. The HRV analyzer 213 performs a Fourier transform (FT), which transforms the HR series from the time domain into the frequency domain, and the resulting power spectrum can be divided into different frequency bands. The power in these frequency bands has been shown to reflect the autonomic state. One example of a frequency domain measurement technique includes analyzing the power in the low frequency (LF, 0.04-0.15 Hz) and high frequency (HF, 0.15-0.4 Hz) bands, measuring their raw power (LF or HF power), normalized power (LFnu or HFnu), or power ratio (LF/HF ratio). Frequency domain measurements may be useful for HR prediction. The overall power is approximately equivalent to the SDNN, and may be used to estimate the overall HR variance. The power and phase of various frequencies may be used to predict the HR trajectory (e.g. rising or falling, based on its sinusoidal phase), so that the BPF can be tuned in advance of upcoming pulses. In performing a frequency domain measurement technique, the HRV analyzer 213 resamples the HR series derived by the beat detector 211 onto an evenly spaced grid. Once resampled, the HRV analyzer executes a fast Fourier transform (FFT) algorithm to transform the resampled data into the frequency domain, to determine the variability of the HR over the window period. Typically, frequency domain measurement techniques require relatively long data windows and assume a stationary time series. This is because the FT basis function, the complex exponential, is highly localized in frequency but poorly localized in time. Accuracy therefore degrades as the window length decreases, so longer analysis windows are desirable.

In a further implementation, the HRV analyzer 213 may determine the HRV measurement value by analyzing the instantaneous HR series data using a joint time-frequency (JTF) domain measurement technique. Using a JTF technique is advantageous because it is designed to operate using an analysis window that is shorter than those used with frequency domain measurement techniques. The frequency domain techniques assume that the HR signal is stationary over the analysis window. However, in reality it is more likely that that HR signal is highly nonstationary. Thus, by using shorter analysis windows a JTF measurement technique can help relieve the stationarity assumption, as the HR series is more likely to approach stationarity as the window shortens. JTF techniques achieve this by providing tunable localization in both time and frequency, adjusting their basis functions to shift energy between the two domains. In so doing, they produce power spectra nearly as precise as pure frequency domain techniques, but with a vastly improved time localization (and thus shorter analysis windows). JTF measurement techniques advantageously respond faster to changes in HRV. Examples of JTF measurement techniques to determine HRV measurement values include, but are not limited to (a) a wavelet transform (WT) which produces results comparable to frequency domain measurement techniques but uses tunable window lengths that can be as short as two samples long; and (b) Wigner-Ville and/or Exponential distributions (WVD & ED) which treat the HR as a stochastic process, and calculate its changing power spectral density over time. In performing a JTF measurement technique, the HRV analyzer resamples the HR signal onto an even grid and then calculates the power in different frequency bands. As before, these can be used to help predict the frequency of upcoming pulses using a plurality of sequential filtering operations to the HR signal to determine the HRV measurement which is used by the filter controller 212 to tune the BPF in advance of upcoming pulses.

In another implementation, the HRV analyzer 213 may determine the HRV measurement value by analyzing the instantaneous HR series data using a nonlinear dynamic measurement technique which detects chaos in the HR series. The nonlinear dynamics of the HR have been shown to change between states of health/relaxation and disease/stress. A chaotic, unpredictable HR has been found to be a marker of good health. Examples of nonlinear dynamic measurement techniques include but are not limited to (a) approximate entropy (ApEn) or sample entropy, which estimate the entropy of the HR series (analogous to information content, statistical surprisal, or unpredictability); (b) Finite time Lyapunov exponents (FTLE), which quantifies chaos from the HR's phase portrait (a graphical map of the changing system states over time); and (c) Detrended fluctuation analysis (DFA), which measures fractal scaling exponents in the HR series. By using nonlinear dynamic measurement techniques, the HRV analyzer may provide a measure of the HR's predictability, allowing for the derivation of a confidence index for use in predicting future pulse times. This confidence index can be output by the HRV analyzer 213 and used by the filter controller 212 to tune the BPF's passband (and included guard band, if applicable). For example, in periods where the HR is less predictable (as evidenced by e.g. increased ApEn), the guard band can be widened to ensure that the filter does not inadvertently reject a future pulse that falls outside the expected frequency range.

Additionally the window used by the HRV analyzer 213 may be selectively modified using a feedback control signal. When analyzing the HRV, the HRV analyzer 213 may selectively control the length of the window representing the amount of HR history that will be included in the analysis window. The HRV analyzer may store a history of HRV measurement values which may be compared to one another to determine a change pattern associated with multiple HRV measurement values. If the stored HRV measurement values are determined to be consistent over a predetermined period of time, the HRV analyzer may automatically shorten the length of the window which would advantageously capture shorter term changes in HRV and also save processing time. Conversely, if the HRV measurement values are changing rapidly, the HRV analyzer may automatically increase the length of the window thereby stabilizing the measurement value provided to the filter controller 212 and used to tune the bandpass filters 208a and 208b. Consistency may be determined in different ways. When using simple statistical techniques (e.g. SDNN, RMSSD), the analysis window length may be set proportional to the rate of change of overall HRV. When using frequency domain or JTF techniques, the analysis window length may be controlled by the relative power in the HF, LF, and VLF frequency bands. For example, if the HR is found to be varying mostly in rapid cycles (strong HF band power, but weak LF and VLF band power), then the HRV analyzer can operate on shorter analysis windows but still capture most of the salient information. Under these conditions the HRV analyzer may automatically shorten the length of the analysis window. Conversely, if the LF or VLF band power becomes significant, then the HRV analyzer may automatically lengthen the analysis windows to capture these slower variations. The consistency may be determined by the rate of change of the relative power between the HF, LF, and VLF frequency bands. When using nonlinear dynamics analysis techniques, the analysis window length may be controlled by the measured predictability of the HR series. If the HR is found to be chaotic (using e.g. FTLE or DFA), or is found to have a high entropy (using e.g. ApEn), then the HRV analyzer may decide that past HR samples offer little information about future samples, and it may automatically shorten the analysis window accordingly.

The HRV measurement value determined by the HRV analyzer 213 using any of the above variability measurement techniques is provided to the filter controller 212 which automatically translates the HRV measurement value into a filter control parameter for use in tuning the bandpass filters 208a and 208b. In one implementation, the filter control parameter includes a set of coefficients that are used by the filter in calculating the frequency envelope to be used by the filter for the upcoming pulsatile measurement thereby defining the passband for the filter. The HRV measurement value is successively calculated on a beat-by-beat basis using a rolling window and the filter controller 212 can similarly successively calculate filter parameters. Thus, the bandpass filters 208a and 208b can be continually tuned on a beat-by-beat basis thereby maximizing the amount of noise rejected while minimizing erroneous rejection of valid pulsatile signal data from the PPG signal. Thus, the HRV measurement value can be used to tune the BPF passband bounds dynamically in time, to capture all of the relevant pulsatile information without being overly broad. In one implementation, the filter parameter calculated by the filter controller 212 may define the upper and lower bounds based on the maximum and minimum HR values observed in a given time window (e.g. ~10 s). In another implementation, the filter parameter calculated by the filter controller 212 may define the upper and lower bounds based on the mean HR combined with the standard deviation of recent HR values (SDNN). In a further implementation, a combination of two or more HRV measurement techniques, as described above, may be used to define the upper and lower bounds or the shape of the frequency envelope. A guard band may optionally be included to hedge against unexpectedly large HR changes, ensuring all relevant pulsatile information passes through the bandpass filters 208a and 208b.

In order to ensure that all relevant pulsatile information in the PPG signal is passed through to the parameter processor 204, the filter controller 212 further advantageously calculates a guard band value. The guard band represents an increase in bandwidth applied to the upper bound and/or a decrease in bandwidth applied to the lower bound of the frequency envelope to ensure that all relevant pulsatile information is passed to the parameter processor 204 without arbitrarily increasing the width of the frequency envelope resulting in passage of PPG signals having noise. In one implementation, the filter controller 212 calculates the frequency envelope and, based on the width of the envelope, calculates a width of a guard band to be applied at the upper and lower bound and generates filter parameter data to tune the bandpass filters 208a and 208b to have a passband with a width equal to the envelope and the guard band. In another implementation, the width of the guard band is predetermined and automatically added to increase the upper bound of the envelope and decrease the lower band of the envelope prior to calculation of the filter parameter used to tune the bandpass filters 208a and 208b.

Feedback may be used by the filter controller 212 to update the HR prediction uncertainty because the HRV measurement value provides an estimate of the upper and lower bounds (and with it the bandwidth) of the HR in the near future (e.g. the next few beats). These estimates will include the guard band representing an additional padding on the upper and lower BPF cutoff limits to hedge against uncertainty in the HR prediction. For example, the recent HRV history may suggest that the HR falls entirely within the range of 90-110 beats/min, and we may predict that this trend will continue in the near future. However, a slight increase in the mean HR may lead to a brief excursion above the upper limit, e.g. at 112 beats/min. Thus, the filter controller 212 may define the width of the guard band at substantially 2 beats/min (or more) which protects against such an excursion and allows for the relevant PPG to pass to the parameter processor 204 for use in determining the PR and $SpO_2$ value for the patient. The guard band does provide an increased opportunity for noise to pass through the bandpass filters 208a and 208b. Thus, the filter controller 212 may advantageously minimize the guard band while also minimizing the risk that the HR will exceed our predicted limits using an active feedback error signal which can help optimize the guard band.

The filter controller 212 may store in a memory, a recent history of HR limit predictions, and compare them to the true HR values as they occur. The filter controller 212 calculates the difference between the predicted HR limits and the actual HR values to generate the error signal which is used as a feedback control to modify the width of the guard band. If the prediction limits consistently overestimate the HR bounds, then the guard band may be reduced. Conversely, if the prediction limits consistently underestimate the HR bounds, then the guard band may be increased. By using the error signal feedback control, the filter controller 212 continually, and in real-time, adapts the width of the guard band to be combined with the frequency envelope which had been determined based on the HRV measurement value. This advantageously enables the system to adapt to the changing uncertainty in the HR predictions.

In another implementation, the system may advantageously determine a signal quality of the first signal sensed by the first sensor (e.g. PPG). In this implementation, parameter processor 204 can also estimate the PR and $SpO_2$ signal quality. The pulse rate (PR) and heart rate (HR) are very similar parameters, but are derived from different source signals. The HR is typically derived from an ECG, while the PR can be derived from a PPG. Their associated characteristics of pulse rate variability (PRV) and heart rate variability (HRV) are likewise very similar. Noise in the PPG can affect the measures of PR and PRV, causing them to differ from their ECG-derived counterparts of HR and HRV. By comparing the PR to HR, and PRV to HRV, the parameter processor 204 can estimate PPG signal quality (with PR and PRV derived pre-filtering) as well as the effectiveness of the filtering scheme (with PR and PRV derived post-filtering). The signal quality can be represented in the form of a signal quality index (SQI) which ranges from e.g. 0 (very poor quality) to 100 (very high quality). The SQI value may be compared to a threshold SQI value and, if the SQI value is below the threshold value, the characteristic analyzer may modify at least one parameter thereof used in determining the variability measurement value. The SQI value can be derived as e.g. a normalized distance between the PR and HR or PRV and HRV measures. A high SQI suggests an accurate measure of PR and $SpO_2$. The description of the SQI provided herein is described for purposes of example only and any manner of providing an indication as to the quality of the signal to a user may be used. For example, the SQI may be provided using a color scheme wherein a first color represents a high quality signal and a second color represents a low quality signal. Any indication scheme may be used to provide the SQI value to the user.

Parameter processor 204 can provide the SQI as an output to subsequent algorithms and/or to the display for the clinician. The clinician can use the SQI to guide him/her in making healthcare delivery decisions. For example, a noisy PPG signal may cause a sudden (false) drop in $SpO_2$. This may appear alarming, but if reported with a low SQI the clinician may decide to wait to ensure it is a true clinical event and not simply the result of noise. Alternatively, the clinician may choose to reposition the sensor or move it to a different site entirely to improve the SQI. Subsequent algorithms can use the SQI to guide them in further analyses (e.g. trend analysis). Parameter values with low SQI may be weighted less heavily than those with high SQI.

The SQI can be used as feedback to the filter controller 212, via the HRV analyzer 213, in the form of an error signal. A low SQI (i.e. a likely inaccurate measure of PR and $SpO_2$) may be addressed by changing filtering parameters and re-deriving the PR and $SpO_2$ values and their associated new SQI value. In one implementation, the monitoring device may optimize the accuracy of the measurements of PR and $SpO_2$ by iterating over successively different filtering parameters, updated based on the SQI error signal. Parameter processor 204 would then report the measured PR and $SpO_2$ values associated with the highest SQI. The optimal filtering parameters may be retained in memory and used as an optimizer starting point in subsequent analysis windows.

Figure 3:
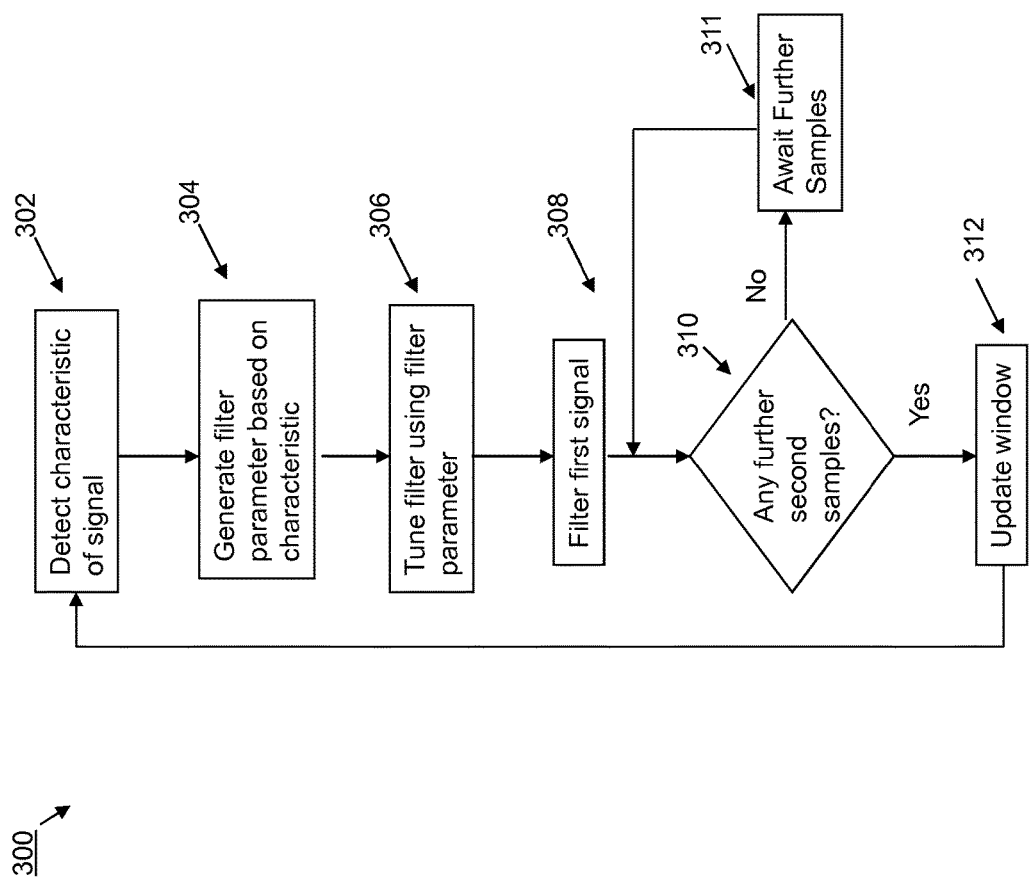
FIG. 3 is a flow diagram detailing an algorithm for reducing noise in a signal.

An algorithm 300 for tuning the filter used to filter a first signal based on a characteristic of a second signal is provided in the flow diagram of FIG. 3. The description of FIG. 3 will make reference to various components of FIG. 1 that are controlled by the algorithm to operate in the manner described. It is also important to note that, although the algorithm is described as a series of linear steps, that certain of these steps may be performed concurrently with one another or in a different order.

In step 302, a characteristic analyzer 110 detects a characteristic associated with a second signal from a window comprising a series of samples received from the second sensor 130. The series of samples in the window represent a predetermined prior period from which the characteristic is determined. In step 304, the determined characteristic is provided to a filter controller 112 which automatically translates the detected signal characteristic into at least one filter parameter representing a frequency envelope. The at least one filter parameter is used to tune a filter 108 by defining the passband of the filter according to the frequency envelope in step 306. In step 308, the filter 108 filters a signal received from a first sensor 120 to allow signals within the passband to be provided to a parameter processor 104 which determines at least one patient parameter data value using the filtered first signal. The algorithm queries, in step 310, whether any successive samples have been sensed by the second sensor 130. If the result of the query is negative, the algorithm awaits any further samples in step 311 which further reverts back to step 310. If the result of the query in step 310 is positive, the algorithm continues at step 312. At step 312, the characteristic analyzer 110 updates the series of signals in the window to include a most recent data value of the second signal and exclude the earliest data value of the second signal. Once the window has been shifted, the algorithm reverts to step 302 and the filter can be continually tuned in real-time to have a passband that maximizes the exclusion of noise and minimizes exclusions of signals relevant in determining the patient parameter data by the parameter processor 204.

Figure 6:
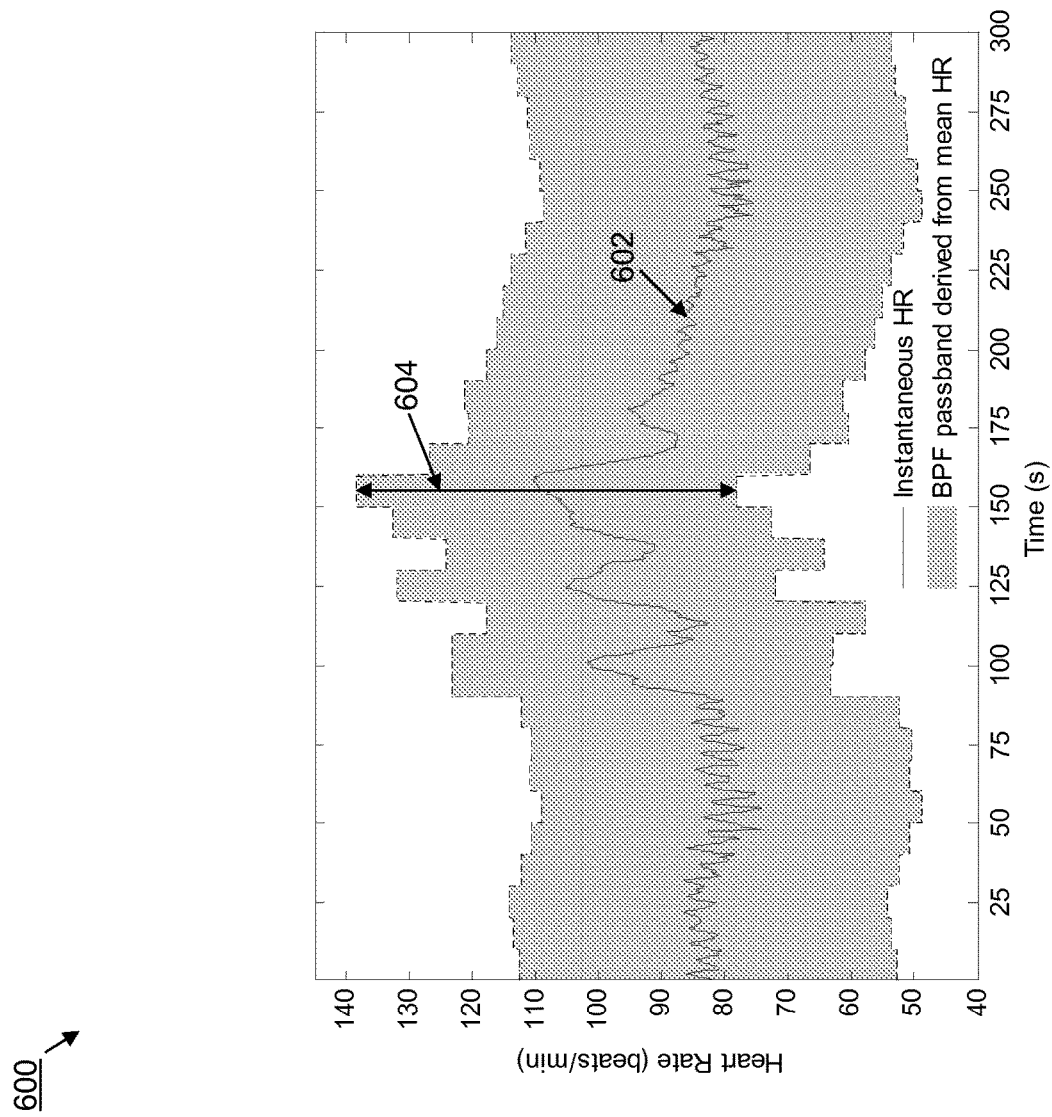
FIG. 6 is a graph depicting an exemplary signal having a frequency envelope used in minimizing noise according to the prior art.
Figure 7:
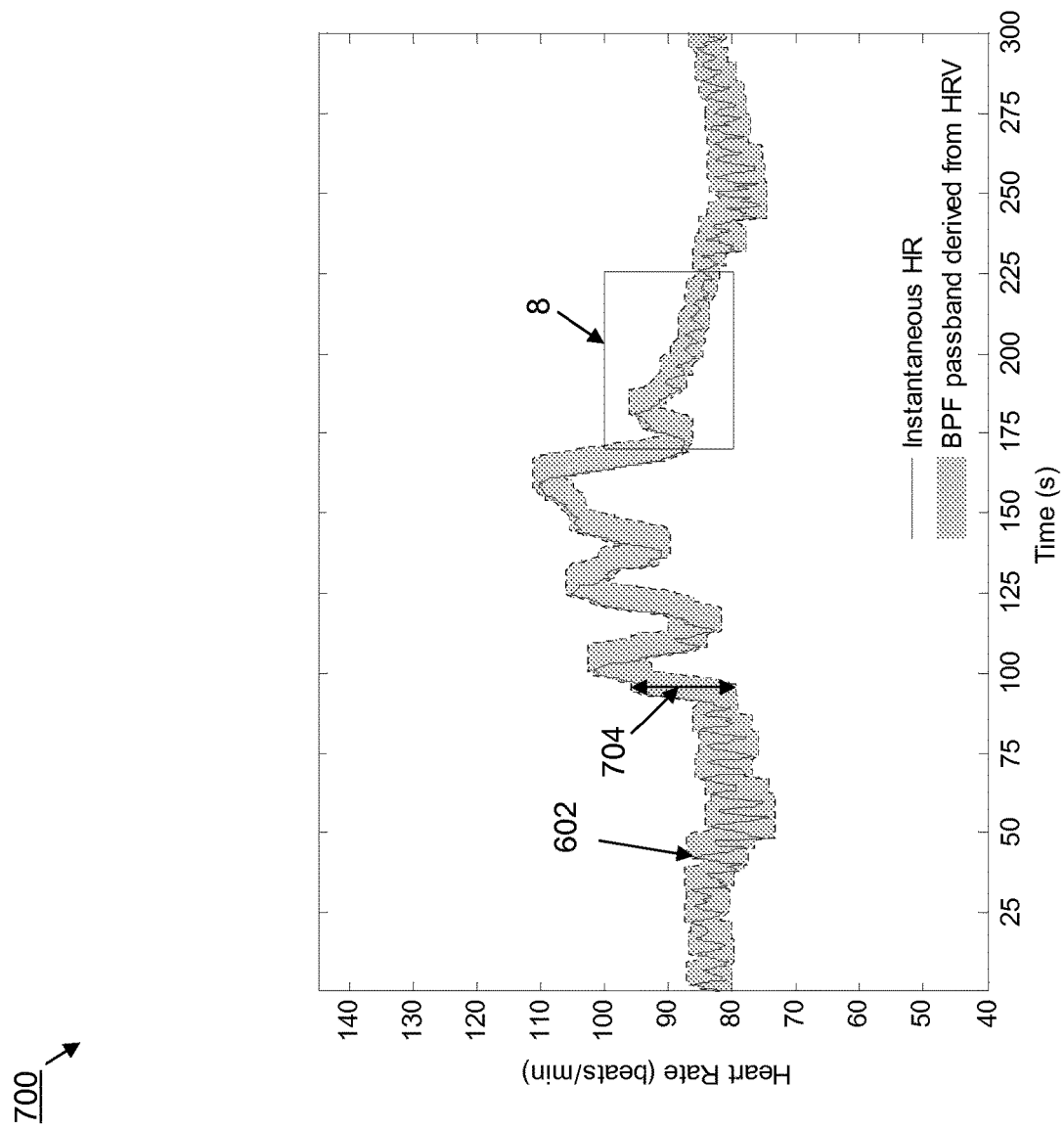
FIG. 7 is a graph depicting an exemplary signal having a frequency envelope used in minimizing noise.
Figure 8:
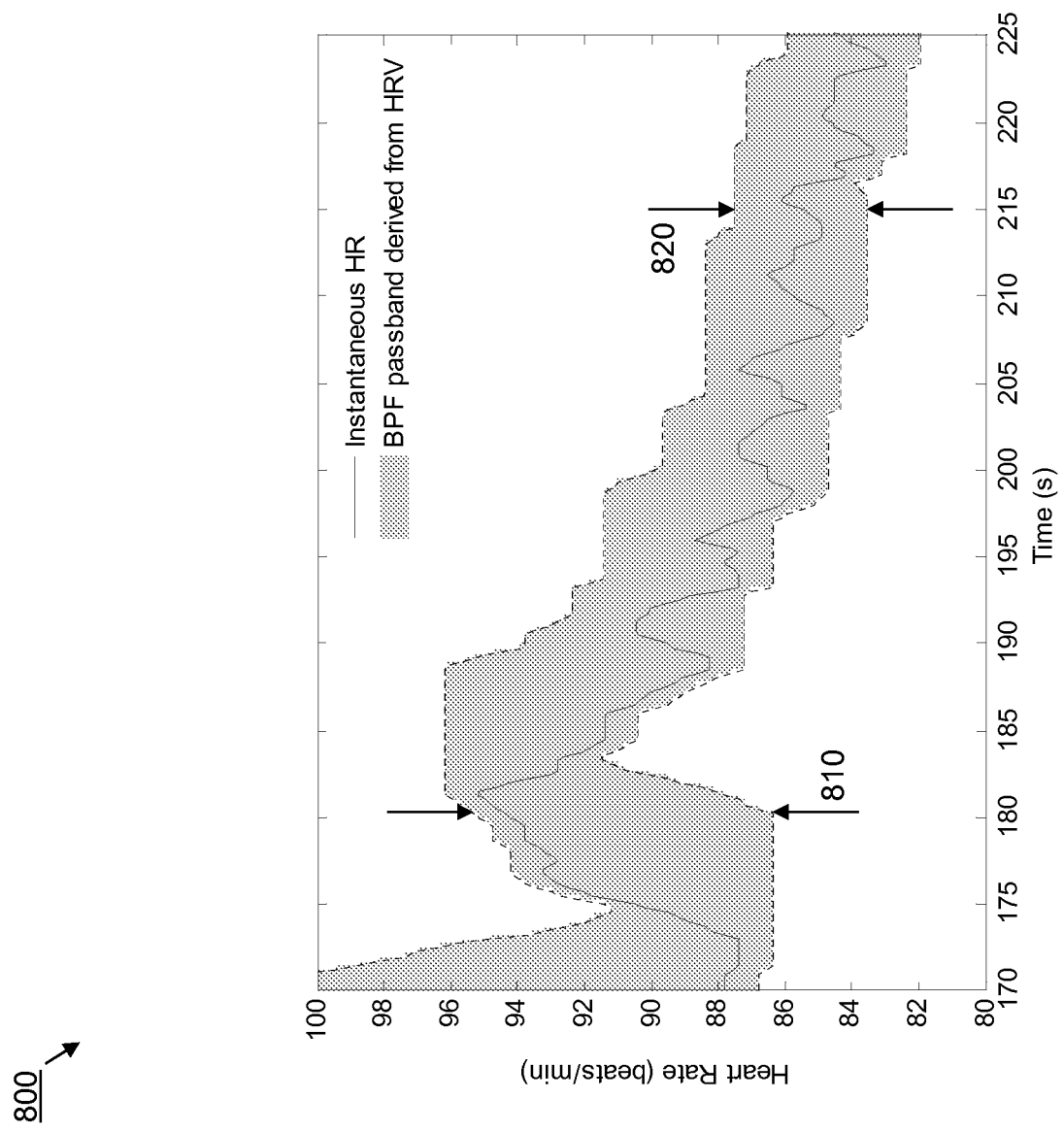
FIG. 8 is a graph depicting a more detailed view of a portion the signal in FIG. 7 showing the frequency envelope used in minimizing noise.

The advantages of using a variability characteristic of one signal to tune a filter for filtering another different signal will be shown in FIGS. 6-8. FIG. 6 depicts a plot 600 of an instantaneous HR in beats per minute over a period of time. The plot of the instantaneous HR is labeled with reference number 602. A gray shadow surrounding line 602 represents the width of the passband that had been determined using a method different from that which is described above in FIGS. 1-5. In an attempt to define the characteristic of the passband, a prior method used is to determine the HR, averaged over a predetermined time period, and to set the BPF center frequency to the averaged HR. Since, in this prior method, the variability of the HR is not used, the method adds a predetermined guard band of ±0.5 Hz (±30 beats/min) to the center frequency thereby defining the passband. The result is a significant increase and decrease of beats per minute around the actual instantaneous HR 602 at any given point. This distance is illustrated by the line labeled 604. Thus, while the passband shown in FIG. 6 rejects noise of very low and high frequencies, the substantial width represented by line or distance 604 allows for a broad range of in-band noise to remain in the filtered signal. The guard band is overly conservative (wide). The HR is unlikely to vary over such a wide frequency range, especially in the short term (~10 s). Thus, such a broad spectrum does not otherwise provide much benefit for deriving patient parameter data (PR and $SpO_2$) because the most relevant information exists at or near the HR. While providing little substantial benefit, this broad spectrum passband does allow a wide window of opportunity for in-band noise to pass through the filter. However, simply narrowing the filter is not an effective solution because this increases the risk of excluding valuable signal components from the patient parameter data calculation. If the HR strays outside the filter's passband at any point in the averaging time window (e.g. ~10 s), the corresponding pulse will be attenuated (partially or wholly rejected) having a destructive effect and leading to incorrect patient parameter data calculations (PR and $SpO_2$ derivations). The result would essentially cause the very problem the narrowing of the passband is trying to solve.

In contrast to the passband set by the method described in FIG. 6, the advantages of the passband set in the plot 700 of FIG. 7 using the variability characteristic to generate the filter parameter used to tune the filter is readily apparent. FIG. 7 includes the same instantaneous HR 602. However, the width of the passband shown in FIG. 7 is determined using the variability characteristic of the second signal. Herein the second signal is an ECG signal and the HRV is determined using any of the HRV measurement techniques described above in FIG. 2. As can be seen in FIG. 7, the distance between the instantaneous HR and the upper and lower bound of the passband indicated by line 704 is substantially reduced as compared to the distance 604 in FIG. 6. The result is a significant improvement in excluding in-band noise but minimizing the exclusion of relevant portions of the first signal being filtered by the bandpass filter. Furthermore, the HRV measurement value is continually updated to allow for real-time continual generation of filter parameters for tuning the filter in order to modify a characteristic (e.g. width and/or shape) of the passband. Therefore, the characteristic (e.g. width) of the passband remains sufficiently narrow to continually reduce the in-band noise.

FIG. 8 is a graph 800 showing a more detailed view of the instantaneous HR over a period of time from which an HRV measurement has been calculated and used to determine filter parameters for configuring the passband of a filter. More specifically, FIG. 8 represents the instantaneous HR shown in FIG. 7 between 170 seconds and 225 seconds represented by the box labeled 8 in FIG. 7. As time increases, we see the dynamic tuning of the passband based on the HRV measurement derived from instantaneous HR from a preceding window of time. Because the tuning is so fine, and the time frame is so large, the width of the passband is virtually indistinguishable from the instantaneous HR plot. The detailed view shown in FIG. 8 shows the instantaneous HR data and compares two points, 810 and 820, which show how different filter parameters can be used to dynamically tune the filter based on a prior period of instantaneous HR data. The passband is much wider at 810 than at 820, based on the recent history of HRV. By tuning based on the variation of the HR over the predetermined period, the filter is able to maximize the amount of relevant signals passing therethrough while minimizing the amount of in-band noise. The method illustrated in FIGS. 7 and 8 sets the upper and lower bounds of the passband to the maximum and minimum HR values (respectively) observed in the previous 30 seconds of instantaneous HR signal. A guard band of ±1 beat per minute is added to the passband bounds. This is a very simple example implementation of the current subject matter principles. More robust implementations employing multiple HRV analysis methods are possible.

Figure 9:
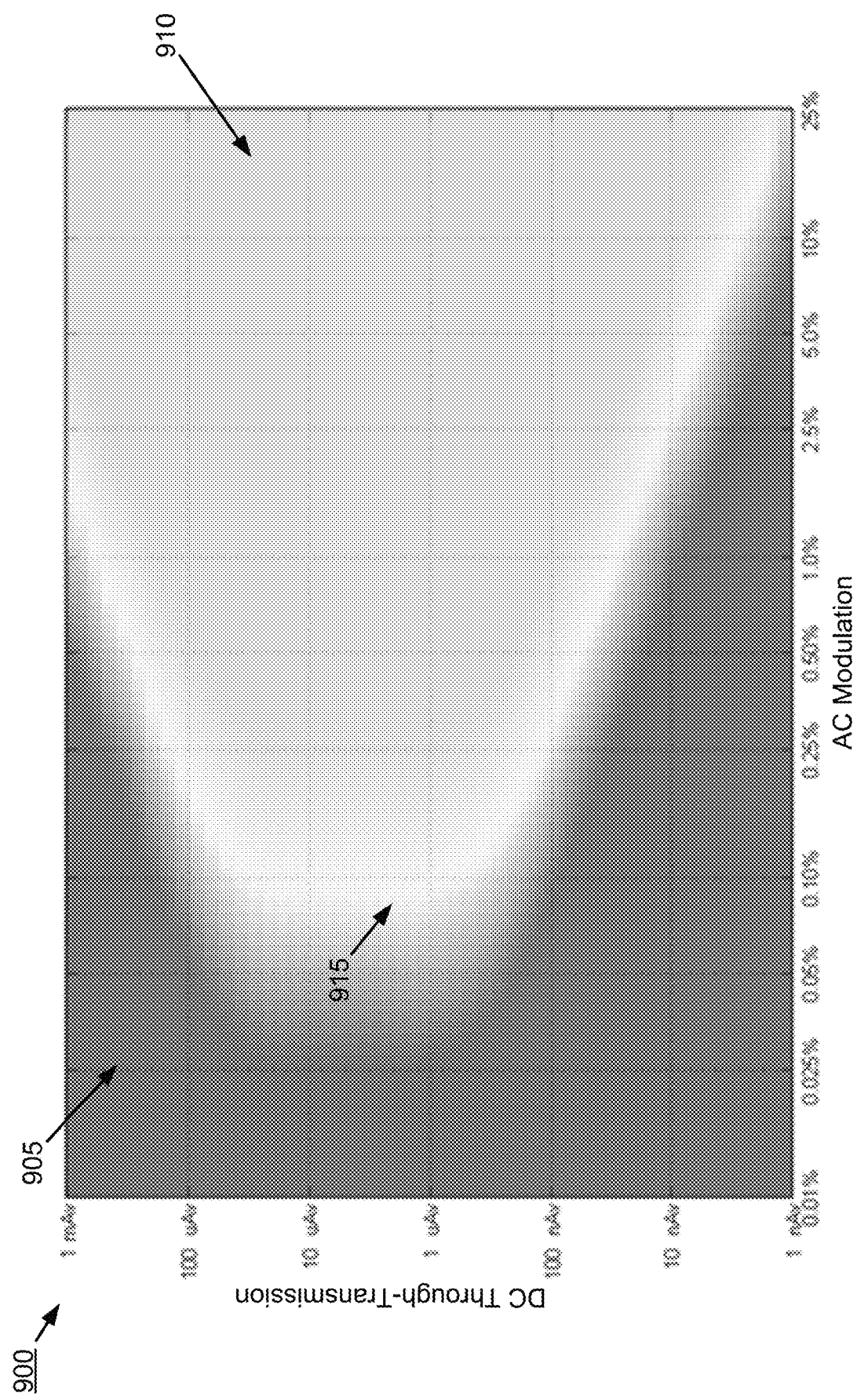
FIG. 9 is a surface map illustrating dynamic range of a pulse oximeter when the PPG signal is filtered with a 5 Hz band pass filter.
Figure 10:
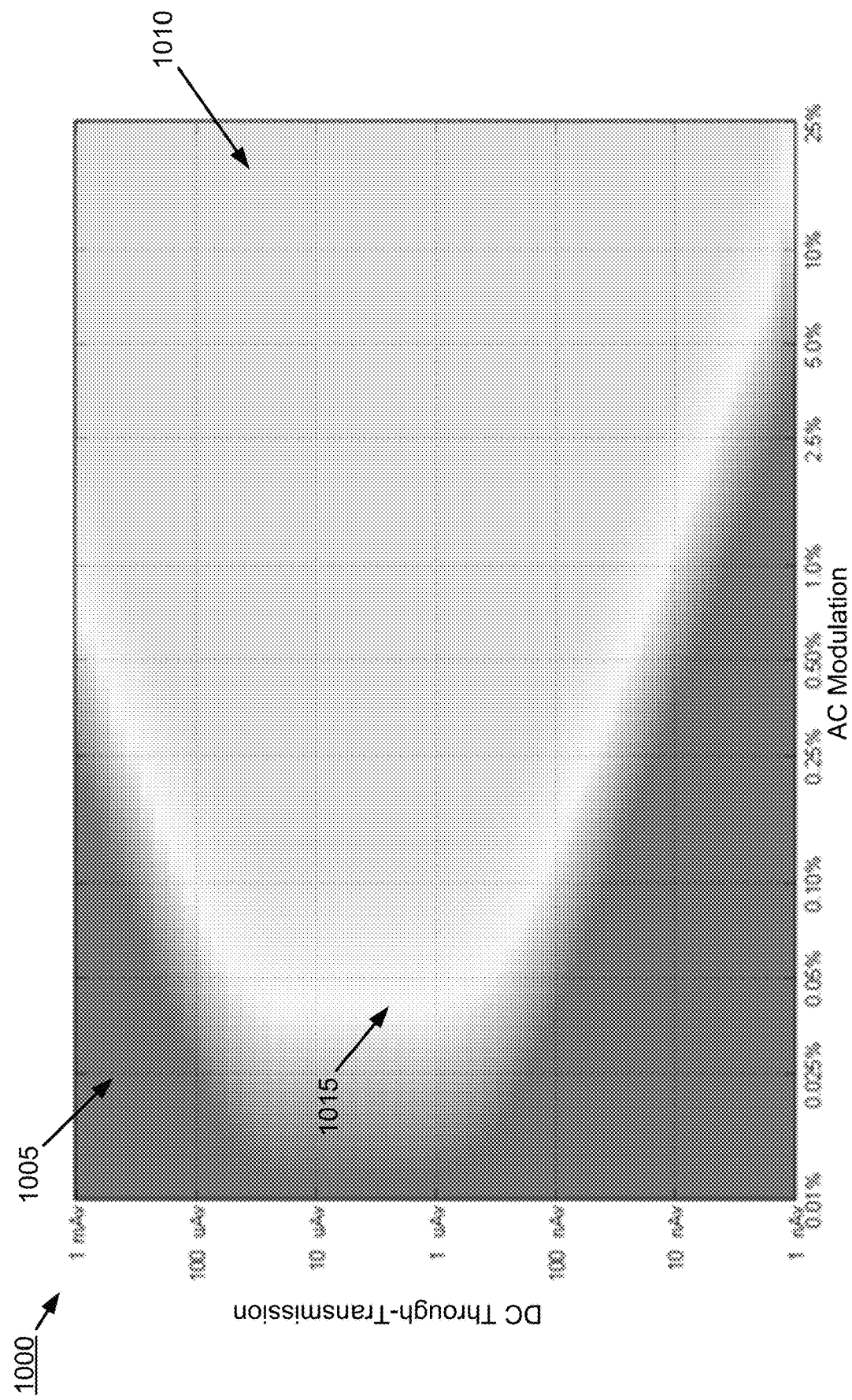
FIG. 10 is a surface map illustrating dynamic range of the pulse oximeter when the PPG signal is band-pass filtered with the BPF center frequency set to the averaged HR with a predetermined guard band of ±0.5 Hz.
Figure 11:
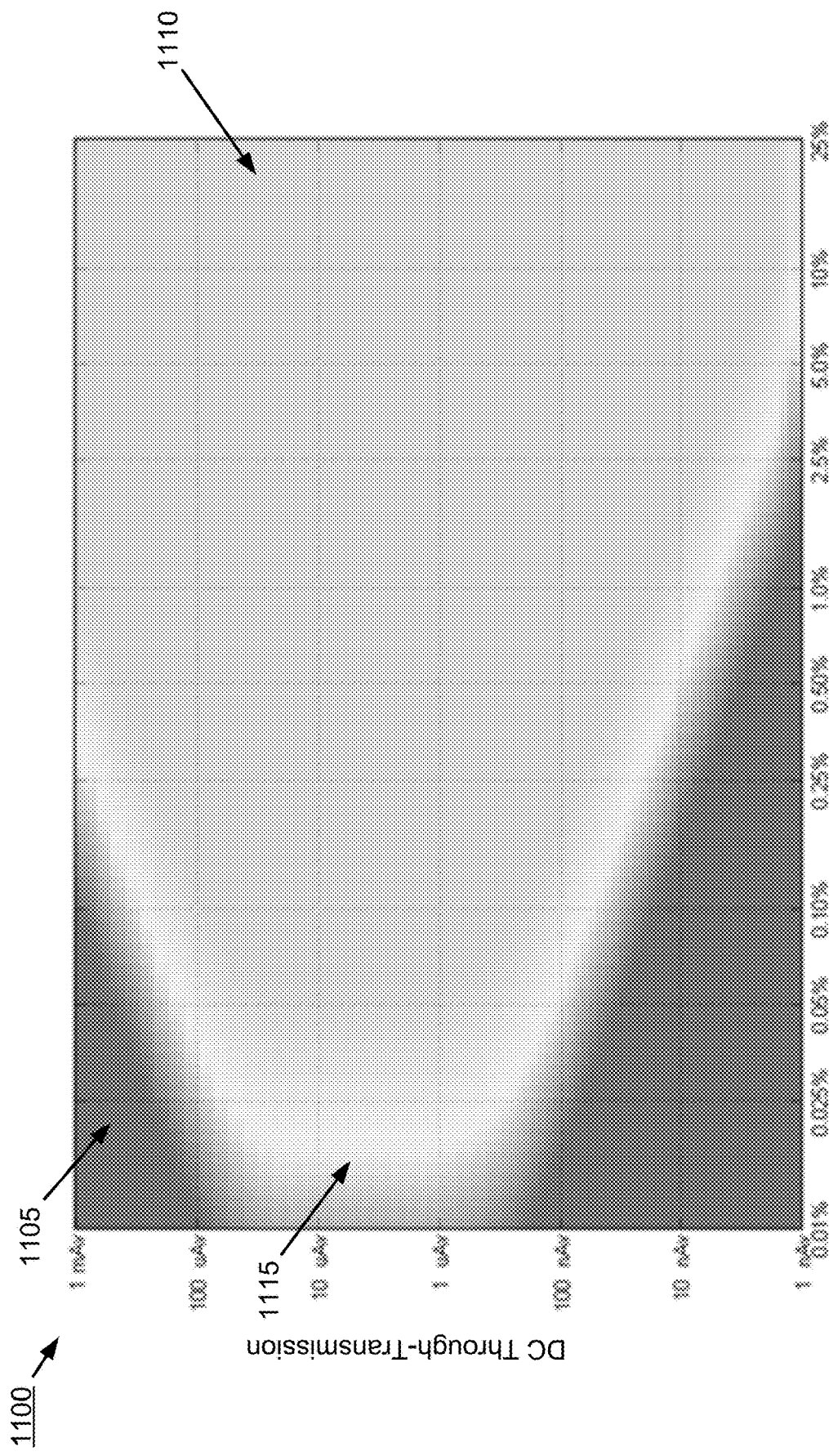
FIG. 11 is a surface map illustrating dynamic range of the pulse oximeter when the PPG signal is band-pass filtered using measures of HRV with a guard band of ±0.1 Hz.

FIGS. 9-11 are surface maps 900, 1000, and 1100 illustrating the dynamic range (e.g., signal to noise ratio performance) of a pulse oximeter when the PPG signal is filtered over the full 5 Hz bandwidth (FIG. 9), when the PPG signal is filtered with the BPF center frequency set to the averaged HR with a predetermined guard band of ±0.5 Hz (FIG. 10), and when PPG signal is band-pass filtered using measures of HRV with a guard band of ±0.1 Hz according to some implementations of the current subject matter. The illustrated data was obtained using a simulation of a pulse oximeter. The vertical axes represent DC through-transmission of the patient's tissue, which is a measure of the transmissivity characteristics of the patient's tissue. The DC through-transmission is shown in units of virtual nanoamperes (nAv), which is defined such that 1 nAv equals 1 nA of receiver input current when the light emitter (e.g., light emitting diode) is driven at 100% intensity (defined as a 50 mA drive current). For example, 1000 nAv=1000 nA at 50 mA emitter drive current, and also 1000 nAv=500 nA at 25 mA drive current.

The horizontal axes represent the AC signal modulation from the patient's arterial blood pulsations. The AC signal modulation from the patient's arterial blood pulsations is a percent modulation of the DC value of the PPG signal. In other words, the AC signal modulation is a measure of the amount of blood in each pulse (which may vary based on physiological conditions such as body temperature). For example, 1% AC modulation of a 1 µAv DC level represents a 10 nAv peak-to-peak AC signal. Thus, both DC through-transmission and AC modulation are properties of the patient and independent of particular pulse oximetry hardware.

Intensity is a measure of signal to noise ratio (SNR) of the PPG signal and indicates the accuracy of the $SpO_2$ measurements. The darker portion on the left side of each of FIGS. 9, 10, and 11 represents lower SNR (denoted by 905, 1005, and 1105, respectively) in which $SpO_2$ measurements will not meet allowed oximetry standards (e.g., accuracy to within more than 2% of true value). The grey on the right side of each figure represents higher SNR (denoted by 910, 1010, and 1110, respectively) which is sufficient for accurate $SpO_2$ measurements (e.g., within 1% of true value). The light portion in the middle of each figure represents SNR values between lower and higher SNR (denoted by 915, 1015, and 1115, respectively) which meets oximetry standards but may still be less accurate ($SpO_2$ accuracy ranges between 1% and 2% of the true value).

FIGS. 9, 10, and 11 illustrate the relative performance improvement for a pulse oximeter utilizing the current subject matter. FIG. 9 contains the largest dark region 905, corresponding to conditions in which the $SpO_2$ measurements are inaccurate and FIG. 10 illustrates dark region 1005 having a slight improvement over the performance of FIG. 9. FIG. 11, which corresponds to a pulse oximeter implemented according to the current subject matter, has the smallest dark region 1105. Thus, an implementation of the current subject provides improvement in SNR for pulse oximetry.

Although the current subject matter has been described in terms of exemplary implementations, it is not limited thereto. Rather, the appended claims should be construed broadly to include other variants and implementations of the current subject matter which may be made by those skilled in the art without departing from the scope and range of equivalents of the current subject matter. This disclosure is intended to cover any adaptations or variations of the embodiments discussed herein.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A patient monitoring device configured to reduce noise in a measured pulse rate signal, comprising:
    a pulse rate sensor operating in a red to infrared electromagnetic spectrum configured to generate a pulse rate signal in response to pulse rate measurements;
    an independently measured heart rate sensor operating outside the red to infrared electromagnetic spectrum configured to generate a heart rate signal in response to heart rate measurements;
    a characteristic analyzer configured to determine a measured heart rate variability based on the heart rate measurements;
    a filter controller configured to dynamically tune an adjustable filter in order to generate a reduced-noise pulse rate signal based on the determined heart rate variability;
    a parameter processor providing a pulse rate output signal based on the reduced-noise pulse rate signal; and
    wherein the characteristic analyzer is further configured to determine a predicted heart rate variability, determine a guard band based of the measured heart rate variability and the predicted heart rate variability, determine a frequency passband for the pulse rate signal based on the heartrate variability and the guard band, and dynamically tune the adjustable filter based on the frequency passband.

2. The patient monitoring device according to claim 1, wherein the heart rate measurements comprises electrocardiogram (ECG) measurements.

3. The patient monitoring device according to claim 1, wherein the characteristic analyzer is further configured to continually determine the measured heart rate variability and continually tune the adjustable filter.

4. The patient monitoring device according to claim 1, wherein the characteristic analyzer continually determines the heart rate variability over successive time intervals and continually adjusts the adjustable filter.

5. The patient monitoring device according to claim 1, wherein the frequency passband comprises at least one of (a) a center frequency; (b) a width of a frequency envelope; (c) lower and upper cutoff frequencies; and (d) a shape of the frequency envelope.

6. The patient monitoring device according to claim 1, wherein the pulse measurements are first pulse rate measurements, further configured for receiving second pulse rate measurements in the red to infrared electromagnetic spectrum; and
    generating the pulse rate signal based on the first and second pulse rate measurements.

7. The patient monitoring device according to claim 6, further configured for:
    computing a blood oxygen saturation level (SpO2) based on measurements the first and second pulse rate measurements; and
    providing a blood oxygen output based on the blood oxygen saturation level (SpO2).

8. The patient monitoring device according to claim 1, further configured for:
    determining a signal quality index (SQI) by calculating a pulse rate variability (PRV) over a predetermined period and comparing the pulse rate variability to the measured heart rate variability; and
    providing a signal quality output based on the signal quality index (SQI).

9. The patient monitoring device according to claim 1, a wherein the parameter processor is further configured to:

determine a signal quality index (SQI) by calculating a pulse rate variability (PRV) and comparing the pulse rate variability to the measured heart rate variability; and provide a signal quality output reflecting the signal quality index (SQI).

10. A method for reducing noise in a measured pulse rate signal, comprising:

receiving pulse rate measurements in a red to infrared electromagnetic spectrum;

generating a pulse rate signal based on the pulse rate measurements;

receiving heart rate measurements, independent of the pulse rate measurements, outside the red to infrared electromagnetic spectrum;

generating a heart rate signal based on the heart rate measurements;

determining a measured heart rate variability based on the heart rate signal;

determining a predicted heart rate variability;

computing a guard band based the measured heart rate variability and the predicted heart rate variability;

determining a frequency passband for the pulse rate signal based on the heart rate variability and the guard band;

dynamically tuning an adjustable filter based on the frequency passband;

determining a reduced-noise pulse rate signal based on the pulse rate signal and the adjustable filter; and providing a pulse rate output reflecting the reduced-noise pulse rate signal.

11. The method of claim 10, wherein the heart rate measurements comprises electrocardiogram (ECG) measurements.

12. The method of claim 10, further comprising continually determining the measured heart rate variability and continually tuning the adjustable filter.

13. The method of claim 10, wherein defining the frequency passband comprises determining at least one of (a) a center frequency; (b) a width of a frequency envelope; (c) lower and upper cutoff frequencies; and (d) a shape of the frequency envelope.

14. The method of claim 10, further comprising dynamically tuning the adjustable filter using at least one of (a) a time domain measurement technique; (b) a frequency domain measurement technique; (c) a joint time-frequency domain measurement technique; and (d) a nonlinear dynamic measurement technique.

15. The method of claim 10, wherein the pulse rate measurements are first pulse rate measurements, further comprising:

receiving second pulse rate measurements in the red to infrared electromagnetic spectrum; and generating the pulse rate signal based on the first and second pulse rate measurements.

16. The method of claim 15, further comprising:

computing a blood oxygen saturation level (SpO2) based on measurements the first and second pulse rate measurements; and providing a blood oxygen output based on the blood oxygen saturation level (SpO2).

17. The method of claim 10, further comprising:

determining a signal quality index (SQI) by calculating a pulse rate variability (PRV) over a predetermined period and comparing the pulse rate variability to the measured heart rate variability; and providing a signal quality output based on the signal quality index (SQI).

* * * * *